(12) United States Patent
Dorn (10) Patent No.: US 11,404,160 B2
(45) Date of Patent: Aug. 2, 2022

(54) METHOD AND SYSTEM FOR MANAGING AND EDITING DATA OF A MEDICAL DEVICE

(71) Applicant: SIEMENS HEALTHCARE GMBH, Erlangen (DE)

(72) Inventor: Karlheinz Dorn, Kalchreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 1085 days.

(21) Appl. No.: 15/025,216

(22) PCT Filed: Sep. 26, 2013

(86) PCT No.: PCT/EP2013/070097
§ 371 (c)(1),
(2) Date: Mar. 25, 2016

(87) PCT Pub. No.: WO2015/043640
PCT Pub. Date: Apr. 2, 2015

(65) Prior Publication Data
US 2016/0239615 A1    Aug. 18, 2016

(51) Int. Cl.
*G06F 16/51* (2019.01)
*G16H 40/20* (2018.01)
(Continued)

(52) U.S. Cl.
CPC ........... *G16H 40/20* (2018.01); *G06F 16/248* (2019.01); *G06F 16/51* (2019.01); *G16H 30/40* (2018.01); *G16H 10/60* (2018.01)

(58) Field of Classification Search
CPC .............................. G06F 19/321; G16H 10/60
See application file for complete search history.

(56) References Cited

U.S. PATENT DOCUMENTS

2010/0036879 A1    2/2010   Friese et al.
2010/0049740 A1    2/2010   Iwase et al.
(Continued)

FOREIGN PATENT DOCUMENTS

CN     102831561 A    12/2012
CN     102982245 A     3/2013

OTHER PUBLICATIONS

Chinese Office Action for related Chinese Application No. 2013800798941 dated Aug. 2, 2017, with English Translation.
(Continued)

*Primary Examiner* — Reginald R Reyes
(74) *Attorney, Agent, or Firm* — Lempia Summerfield Katz LLC (57) ABSTRACT

The invention relates to a method and to a system for managing and editing data of a medical device (2, 2'). According to the invention, separate memory areas (22-25) in a cloud storage (19) of a public cloud (13) are provided for at least two different types of medical data sets (P, W, C, B). The data sets (P, W, C, B) stored in a particular memory area (22-25) are each held available in such a way that said data sets (P, W, C, B) can be directly accessed from the Internet (16) if a subscription (18, 18) associated with the memory area (22-25) exists. In addition, at least one specifically associated application (31-34, 94, 95) for running on a user device (8, 9, 11, 12) is provided for each memory area (22-25), said application being designed to retrieve and/or display the data sets (P, W, C, B) contained in the associated memory area (22-25).

14 Claims, 7 Drawing Sheets

(51) Int. Cl.
*G06F 16/248* (2019.01)
*G16H 30/40* (2018.01)
*G16H 10/60* (2018.01)

(56) References Cited

U.S. PATENT DOCUMENTS

| | | |
|---|---|---|
| 2010/0332401 A1 | 12/2010 | Prahlad et al. |
| 2012/0233668 A1 | 9/2012 | Leafe et al. |
| 2013/0006865 A1* | 1/2013 | Spates .................. H04L 9/083 705/50 |
| 2013/0024917 A1* | 1/2013 | Han ....................... G06Q 10/10 726/5 |
| 2013/0185331 A1* | 7/2013 | Conemac ............... G16H 30/20 707/783 |
| 2013/0208966 A1 | 8/2013 | Zhao et al. |
| 2015/0234557 A1* | 8/2015 | Dorn ........................ G06F 8/24 715/803 |

OTHER PUBLICATIONS

Bahga et al; "A cloud-based approach for interoperable electronic Health records (EHRs)," IEEE Journal of Biomedical and health informatics, IEEE, bd. 17, nr. 5, pp. 894-906, ISSN: 2168-2194, DOI: 10.1109/JBHI.2013.2257818, XP011525485, 2013.

Benjamin et al., "From shared data to sharing workflow: Merging PACS and teleradiology," European Journal of Radiology, Elsevier, bd. 73, nr. 1, pp. 3-9, ISSN: 0720-048X, XP026832170, 2010.

Patel et al., DICOM Medical Image Management the challenges and solutions: Cloud as a Service (CaaS), Computing Communication & Networking Technologies (ICCNT), third international conference on IEEE, pp. 1-5, DOI: 10.1109/ICCCNT.2012.6396083, XP032443043, 2012.

* cited by examiner

METHOD AND SYSTEM FOR MANAGING AND EDITING DATA OF A MEDICAL DEVICE

CROSS-REFERENCE TO RELATED APPLICATION

This application is the National Stage of International Application No. PCT/EP2013/070097, filed Sep. 26, 2013, the entire contents of which are hereby incorporated herein by reference.

REFERENCE TO A COMPUTER PROGRAM LISTING APPENDIX SUBMITTED AS AN ASCII TEXT FILE

The present application hereby incorporates by reference the entire contents of a computer program listing appendix, submitted via the USPTO's electronic filing system in ASCII format, that includes three examples of computer program code. Each example is labeled as "Annex 1," "Annex 2," and "Annex 3," respectively. Annex 1 includes example code for a user interface of a container, Annex 2 includes example code for logic of a container. Annex 3 includes the three separate examples, labeled "Annex 1," "Annex 2," and "Annex 3," respectively, in a single text file named "2013P02047WOUS_11371-16016A_computer_program_listing_appendix.txt," created on May 25, 2022, last modified on May 26, 2022, having a file size of 46,349 bytes.

BACKGROUND

The present embodiments relate to a method for managing and editing data of a medical facility and a system for carrying out this method.

Here and below the term "managing" is, for example, taken to mean the archiving of data (i.e., putting the data in a persistent data memory), the reproduction (display) and deletion of data from the data memory and sorting and locating specific data from the data memory according to predefined criteria (browsing).

Here and below the term "editing" is, for example, taken to mean the revision (editing/rehashing) of the data.

The data, which is to be managed and edited, of the medical facility includes, for example, patient data, tasks (works/tasks) or worklists for the staff of the medical facility, and medical image data.

Medical data of this kind is increasingly managed in a computer-assisted manner by server systems (e.g., what are known as information systems). An information system regularly includes
  one or more data memory (memories), for example in the form of a Storage Area Network (SAN),
  one or more associated data servers,
  at least one relational database which is implemented in a database server,
  and, as a rule, one or more further server(s) in which methods for database access and data processing are implemented.

Different information systems have established themselves in the medical sector for the different types of data. Therefore, in the environment of a medical facility such as, for example, a hospital, a "Hospital Information system" (HIS) for managing and editing the patient data and a "Radiology Information System" (RIS) for scheduling radiological examinations, aiding diagnosis of medical image data and documentation of the findings are regularly used. In addition the IT structure of a hospital as a rule includes what is known as a "Picture Archiving and Communication System" (PACS) for archiving and transmitting medical image data on the basis of the DICOM standard, and an "Advanced Visualization (AV) system," which provides server-assisted functions for visualizing volume data (e.g., dynamic volume rendering).

The server systems denoted above are, as a rule, present simultaneously. This requires high acquisition and maintenance expenditure which, for small medical facilities or other facilities with comparatively low finance volume, for example, is difficult to cope with.

The complex IT structure of a modern medical facility described above also has comparatively poor scaling properties. Adjustment of an IT structure of this kind that includes significant changes in the data volume to be processed and archived, and/or the required computing power is therefore usually only possible with very high expenditure.

Personal Computers (PCs) are predominantly used as the user devices or end devices (conventionally called clients) of an IT structure of this kind, wherein these PCs are often designed as what are known as "Thin Clients" that draw a large part of the required computing power from a connected server.

In the past few years what are known as cloud solutions have established themselves as an alternative to conventional client-server architectures. The "cloud" is in this connection taken to mean a data processing mechanism that is provided and operated by a cloud vendor that is independent of the user. As a service, the "cloud vendor" provides a large number of users with the hardware and optionally the software of the cloud within the framework of a subscription. Depending on the extent of the services provided, a distinction is made between different usage patterns.

In one usage pattern called "Infrastructure as a Service" (IaaS), the user is only provided with computer hardware (computers, networks and storage) of the cloud whereas the user himself is entirely responsible for the software operated in the cloud.
  In another usage pattern described as a "Platform as a Service" (PaaS), the user is provided with the computer hardware together with a programming and runtime environment that builds thereon from the cloud, so the user himself is only responsible for the application software (applications) implemented in this programming and runtime environment.
  In another, usage pattern called "Software as a Service" (SaaS), the user is also provided with specific application software from the cloud.

Depending on the user group to which the respective cloud is addressed, a distinction is made, moreover, between
  what is known as a public cloud, whose services can be used by anyone, and
  what is known as a private cloud that only users of a specific organization (e.g., a specific concern) can access.

For each user of a public cloud, the access rights to specific hardware and software components of the cloud are regulated by the subscription associated with the user. Public clouds are regularly "multi-client capable" (multi-tenant) as a result. This denotes the capability to keep data, user management, and computing operations strictly separate for users with different subscriptions. One user of the public cloud therefore cannot look at the data, user management, and computing operations of a different user with a different subscription and cannot manipulate this data either.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method and a system for managing and editing data of a medical facility, which can be used especially flexibly (e.g., especially scalable) are provided.

According to the present embodiments separate memory areas respectively are provided in a cloud storage (i.e. the persistent memory) of a public cloud for at least two different types of data of the medical facility, wherein the data sets stored in the respective memory area are held available in such a way that said data sets can be directly accessed from the Internet if a subscription associated with the memory area exists (if, in other words, the accessing device has authorization access according to the subscription).

This access option is, for example, designed such that it is compatible with the Representational State Transfer (REST) Internet standard. REST denotes a programming paradigm for Internet applications that satisfies the following principles: a unique address (Uniform Resource Locator, URL for short) is allocated to each service offered, the service that can be accessed under an address can have different manifestations (representations); a (stateless) client-server protocol is used which enables different queries between clients and server to always be dealt with independently of each other; it must be possible to apply a predefined number of operations (namely, for example, the four operations GET, POST, PUT, DELETE) with defined properties to all resources; and multimedia hypertext (hypermedia) is used for both application information and for status changes.

Representation may occur according to the XML (Extensible Markup Language), JSON (Java Script Object Notation) and/or ATOM Internet standards. ATOM is used as an umbrella term here for the Atom Syndication Format (ASF) which is an XML format for the exchange of messages, and the ATOM Publishing Protocol (APP) which is a programming interface for generating and editing web contents.

The medical facility, with which a subscription is associated in each case, is a hospital in the primarily targeted application. However, within the context of the present embodiments, it is also conceivable for smaller units, such as, for example, medical practices, individual departments of a hospital or even individual patients, to acquire a separate subscription for managing the respectively separate medical data and to therefore be able to use the disclosed method or system in full.

The system is in this connection "multi-client capable" (multi-tenant) due to the use of the public cloud within the meaning described above. Data, user management and computing operations are therefore kept strictly separately from each other for users with different subscriptions. Thus, looking at or manipulating data of external subscriptions is ruled out.

Within the context of the disclosed method and system an application is furthermore provided for running on a user device or end device (hereinafter called a "device") for each memory area. The application is configured to retrieve and/or display the data sets contained in the associated memory area.

Each application is specifically associated with precisely one of the memory areas and therefore selectively and only implements those functions for managing and editing the data sets contained in the respective memory area.

The different types of data of the device includes, for example:
patient data, including personal and medical details on a specific patient of the facility (e.g., details on the name, address, age, gender, earlier diagnoses and treatments); tasks (works/tasks) and worklists that are to be carried out by one or more medical user(s) (physicians, medical assistants, care givers, etc.) of the medical facility; medical image data (e.g., two-dimensional images, two-dimensional image sequences (videos), volume data (e.g. computer tomograms) and/or temporal volume data sequences (4D data), but also key images, photos, documents and the like); and context information relating to medical image data, such as, for example, references to the storage location of image data sets and optional metadata relating to image data sets such as, for example, the recording parameters underlying the respective scan.

A "key image" denotes here a snapshot, i.e., a(n) (edited or unedited) detail from a medical image data set or volume data set which is derived during diagnosis of this data in order to depict a medical finding. Key images of this kind are typically used as a component of a medical report (reports).

Each of these different types of data will hereinafter also be called a "resource". The memory area of the cloud storage respectively allotted to this resource will hereinafter also be called a "(resource) hub". In one embodiment, at least two of the (resource) hubs listed below are provided in cloud storage in allocation to the above-described resources within the context of the method and system:
a patient memory area (patient hub) in which each (patient) data set contains patient data of a specific patient; a worklist memory area (worklist hub) in which each data set contains a task (work/task) or worklist; an image data memory area (image hub) in which each (image) data set contains medical image or volume data or another item of image, sound, graphics or text information (photos, videos, documents); and/or a context memory area (context hub) in which each (context) data set contains context information relating to an image data set, such as, for example, a reference to the memory location of the respective image data set in the image hub, and optional metadata relating to the image data set.

Each of the above-described hubs, together with the application specifically associated therewith, can be operated independently (i.e., independently of the other hubs and the applications respectively associated therewith). Therefore, none of the above-described hubs or the associated applications is imperative for carrying out the disclosed method or within the context of the disclosed system. However, each of the above-described hubs, together with the associated application, advantageously expands the functionality of the disclosed method or system.

The present embodiments start from the consideration that for reasons of improved scalability for data management and editing in a medical facility, a change from a conventional client-server solution through to a cloud-based solution is expedient. As is known, however, the problems described in the Background section are not satisfactorily solved by merely transferring the conventional server systems into the cloud. Transferring the servers conventionally used in a medical facility into the cloud does not simplify the complexity of the IT structure. Instead, it tends to increase it, especially since the servers in a cloud are regularly operated in a virtualized form, and therefore the virtualization software would also be added to the complex server structure which is unchanged. In addition, as is known, with a solution of this kind high costs would arise for the server performance (Cloud Virtual Server) rendered in the cloud, and these would largely offset the advantages of cloud use. Furthermore, the virtualized servers operating in the cloud would still have to be administrated by the facility itself, so the expenditure associated therewith would remain. A solution of this kind would not bring any significant improvement in respect of scalability and reliability either.

Such an improvement is achieved, however, by the disclosed idea of storing the medical data in the public cloud storage such that said data can be accessed—for example in a REST-compatible manner—via the Internet. This enables at least a large part of the computing power required for carrying out the disclosed method to be generated in the devices themselves which are involved in carrying out the method. Therefore, in the course of the disclosed method solely, or at least almost solely, the—comparatively inexpensive—cloud storage of the public cloud is used, whereas the significantly more expensive computing power of the public cloud (cloud compute services) are not used, or are only used to a small extent. The sole, or at least almost sole, allocation of the computing power to the devices also contributes to a significantly improved scalability of the disclosed method and the associated system since the structures implemented by the cloud do not have to be adapted to a changed required for computing power. For example, no virtual servers have to be acquired and maintained in the cloud. Instead, the optionally used cloud compute services are maintained and provided directly by the cloud provider within the meaning of a PaaS concept.

The distribution of the various resources among different resource hubs that are completely separate from each other, and the provision of the applications specifically associated with these hubs in each case enables particularly flexible use of the disclosed method and of the associated system, especially since different medical facilities can freely select the hubs contained within the framework of their respective subscription without having to take into account mutual dependencies. The costs for operation of the disclosed method and the associated system can in turn be flexibly regulated hereby for the medical facility.

By using the public cloud for archiving and holding the data available the medical facility benefits from the conventional advantages of public cloud storage, namely almost unlimited scalability (i.e., the possibility of efficiently managing almost any volumes of data without qualitative changes to the IT structure), global availability of the data, extremely high security against failure and manipulation and a virtually complete reduction in the acquisition and maintenance expenditure within the facility.

To summarize, the present embodiments disclose an IT structure that is completely different from the norm in the medical sector. It enables the advantages of a public cloud over a conventional client-server solution to be efficiently used without having to accept appreciable drawbacks in the process.

The "Windows Azure" service belonging to Microsoft may be used as the public cloud. Other public clouds can also be used within the context of the present embodiments, however. For example, a plurality of public clouds from optionally different "cloud vendors" can also be used (simultaneously) for managing the data of the facility.

The devices of the facility that are involved in carrying out the disclosed method can be desktop PCs in any desired structure, but also mobile devices such as notebooks, tablet computers and smartphones.

The applications may be configured to directly access the data sets contained in the respectively associated hub. Additionally or alternatively, the applications may be configured to directly generate, edit and delete the data sets contained in the respectively associated hub. The term "directly" is respectively used here and below in the sense that the application executes the respective action independently solely using cloud storage without—independently of pure storage management (cloud storage)—computing power of the public cloud (cloud compute services) being used for this.

At least one of the applications may be operated in two operating modes within the context of the present embodiments, however, namely
  in a "device only mode" in which the application runs solely on one device, accesses the cloud storage directly and does not use cloud compute services of the public cloud, and
  in a "cloud service mode" in which the application also uses cloud compute services of the public cloud to access and/or display the data sets contained in the hub.

This—optionally switchable—cloud service mode is provided, for example, in what is known as a 3D viewing application which is used for—particularly computing power-intensive—displaying of rendered views (scenes) of volume data. The computing power is provided by the cloud vendor, for example, within the framework of a PaaS usage pattern, so no separate administration costs accrue for the operating system, driver, an application server (App Store) and the like.

Within the context of the present embodiments, it can be provided that the choice between the device only mode and the cloud service mode is
  made either automatically by the application (for example as a function of the quality of the network connection and/or the computing capacity of the device),
  determined interactively by the medical user, or
  defined by pre-setting (configuration data) of the application.

In one embodiment, table storage may be set up within at least one hub. This is taken to mean a form of data storage—for example provided as standard within the framework of Microsoft's "Windows Azure" service—in which data entities are stored in a structured manner together with an index variable, which clearly identifies each data entity, as table entries. In the case of the "Windows Azure" service this index variable is composed, for example, of what is known as a PartitionKey and what is known as a RowKey. The PartitionKey designates a physical partition of the cloud storage in which the respective table entry is stored, so table entries with a different PartitionKey are stored in different physical partitions.

Within the table storage one table entry (hereinafter called a "tweet") is allocated to each of the data sets stored in the respective hub. Each tweet can contain the associated data set itself. Each set of patient data of the patient hub may therefore be stored as a tweet of the associated table storage. Alternatively (such as, for example, in the case of data sets having large and/or non-alphanumeric data blocks, (e.g. medical images)), the data set itself is stored externally to the table (outside of a table storage), for example in what is known as a blob storage of the cloud storage. The tweet allocated to the data set in this case contains an indication of the storage location external to the table, for example in the form of what is known as a "Uniform Resource Identifier" (URI). Again, as an alternative to this, specific data blocks of a data set can be stored within the framework of the tweet in the table storage while at least one further data block of the same data set is stored external to the table. Therefore, for example in the case of medical image data sets, the actual image data is expediently stored in a blob storage of the image hub while the associated metadata (e.g., recording parameters and details on the patient) is stored within the framework of the associated context information in the table storage of the context hub. Blob storage, as is likewise provided as standard within the framework of Microsoft's "Windows Azure" service, denotes a form of data storage in which there is unstructured storage of data sets.

According to the disclosed method the application associated with the hub may search through content of the table storage directly (without using computing power of the public cloud, i.e. cloud compute services). As a result of this search selected tweets are extracted in the form of a results list which is displayed by the application. A results list of this kind is called a "feed" below.

The above-described embodiment of the applications and of the disclosed method carried out by it enables effective "browsing", i.e., effective sorting and locating the data stored in the respective hub, without having to use computing power of the public cloud, i.e., cloud compute services, for this.

In one embodiment, the feed extracted from the associated hub by the application is "externalized" by at least one of the applications, i.e., is downloaded from the public cloud storage into a local memory of the device, so, even without a network connection to the public cloud, this feed and the tweets contained therein may be displayed, edited and/or transmitted by the application to a different instance of the same or a different application by the application.

This exchange mechanism (also called an "exchange board") enables particularly effective and flexible communication between different application instances which again manages without computing power of the public cloud, i.e., cloud compute services. For example, the URI of an image to be viewed can in this way be ascertained and transmitted to a viewing application of the image hub separate therefrom by a browsing application associated with the context hub, so the viewing application may then independently access the image being sought using the URI. This exchange may also readily occur between different devices, for example by sending the tweet associated with the image data set or/or the URI contained therein via email, instant message or Twitter.

In a further advantageous development of the disclosed method and system modalities of the medical facility (i.e. the imaging devices, such as, e.g., computer tomographs, magnetic resonance tomographs, etc.) are also revamped for direct communication with the cloud storage. During the course of the method a medical modality therefore generates a data set, containing patient-specific image data, and stores it directly in the associated memory area (e.g., the image hub) of the cloud storage. This functionality for direct communication with the public cloud storage is implemented, for example, in a storage driver that provides the control software of the modality within the framework of an Application Program Interface (API for short). The storage driver may be directly integrated in the control software of the respective modality. Alternatively, the storage driver may form a stand-alone program component that the control software of the modality accesses in the manner of a printer driver. The above-described embodiment of a modality for directly loading the image data sets generated by the modality into an associated memory area (image hub) of public cloud storage is regarded as a stand-alone embodiment that may advantageously also be used without the remaining features of the above-described method or system.

The disclosed system for managing and editing data of a medical facility is configured in terms of circuitry or programming to carry out the above-described method. For this purpose it includes at least two (resource) hubs of the type described above for storing at least two resources (i.e. two different types of medical data sets), with each hub being assigned only the data sets of a specific resource. The data is held available in the respective hub such that said data can be directly accessed from the Internet if a subscription associated with the hub exists. Associated with each hub is at least one application that is selectively configured to retrieve and display the data sets contained in the associated hub. The variants described above in conjunction with the disclosed method and the advantages associated therewith should logically be transferred to the disclosed system.

In the narrower sense the disclosed system includes only said memory areas (hubs), the associated applications and optionally the above-described storage driver. The system is in this sense formed solely from software components. In a wider sense the disclosed system also includes the cloud storage that is a hardware memory with cloud-internal administration software running thereon, and at least a device that is connected to the public cloud storage via the Internet. The device is, for example, a personal computer (PC), notebook, tablet computer or a smartphone.

BRIEF DESCRIPTION OF THE DRAWINGS

Exemplary embodiments of the present disclosure will be illustrated in more detail below with reference to drawings, in which.

Mutually corresponding parts and variables are provided with the same reference characters in all figures.

DETAILED DESCRIPTION

Figure 1:
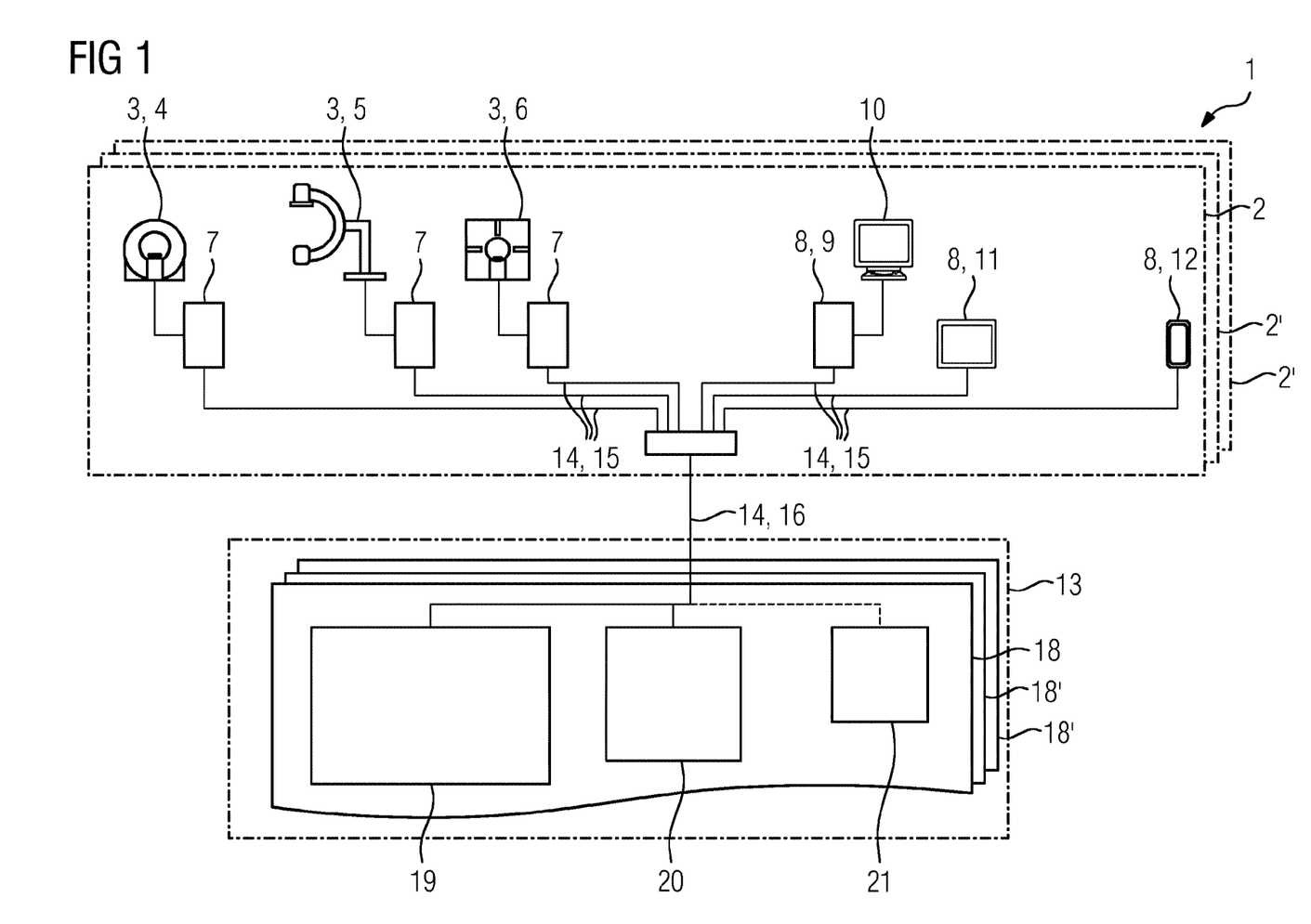
FIG. 1 shows in a schematic block diagram a system for managing and editing data of a medical facility, having a plurality of modalities and user devices or end devices (devices) and having a public cloud connected to the modalities and devices via the Internet.

FIG. 1 shows in a rough schematic simplification a system 1 for managing and editing medical data of a medical facility 2 which is, for example, a hospital.

In terms of hardware, the system 1 includes a number of modalities 3, i.e., imaging and medical examination equipment of the facility 2. The system 1 in the exemplary view according to FIG. 1 therefore includes a computer tomograph 4, a C-arm device 5, and a magnetic resonance tomograph 6. A (control and evaluation) computer 7 is associated with each modality 3.

In terms of hardware the system 1 also includes a number of user devices or end devices (hereinafter devices 8) of the facility 2 that are used for displaying and editing data. In the simplified example according to FIG. 1 the devices 8 include a personal computer 9 with connected screen 10, a tablet computer 11 and a smartphone 12.

As a component arranged outside of the facility 2 the system 1 includes a public cloud 13. The service provided by Microsoft under the name "Windows Azure" for example is used as the public cloud 13 within the context of the system 1. In another embodiment a different public cloud or a combination of a plurality of public clouds (optionally also from different providers) may also be used as the public cloud 13 within the context of the present embodiments, however.

The public cloud 13 is connected by a (data transfer) network 14 to the components of the system 1 that are internal to the facility, i.e., the modalities 3 and devices 8. Within the facility 2 this network connection is formed inside by an Intranet 15 of the facility 2 which is constructed, for example, as what is known as a Local Area Network (LAN) on the basis of wired Ethernet technology and/or as a Wireless Local Area Network (WLAN). Outside of the facility 2 the network 14 is formed by the Internet 16. A firewall 17 is conventionally arranged at the interface between the Intranet 15 and Internet 16.

The services provided by the public cloud 13 within the context of the system 1 are defined by a usage contract called a subscription 18. The subscription 18 regulates which hardware and software components of the public cloud 13 the components of the system 1 that are internal to the facility can be accessed. Therefore, the term subscription 18 will hereinafter denote the part of the public cloud 13 that is exclusively associated with the facility 2 within the context of the system 1. Other regions of the public cloud 13 may—as indicated in FIG. 1—be allocated within the framework of further subscriptions 18' to further medical facilities 2'. Each facility 2, 2' has access solely to the data and services allocated to it in accordance with its subscription 18,18', but not to the data and services of other facilities 2 or 2'. The public cloud 13 is in this case "multi-client capable" (multi-tenant).

According to the subscription 18, the system 1 of the facility 2 within the public cloud 13 is provided with data storage hereinafter called cloud storage 19, storage for applications (application software) hereinafter called an App Store 20, and cloud compute services 21.

The cloud storage 19 is used for persistent storage of the data of the facility 2. The App Store 20 provides applications, drivers and other peripheral software, such as, for example, configuration data files and templates, which may be downloaded by the components of the system 1 that are internal to the facility, i.e., the modalities 3 and the devices 8 and run on the modalities 3 (more precisely, the associated computers 7) or on the devices 8 during operation of the system 1. Within the framework of the system the cloud compute services 21 are used purely optionally for all computing operations that are not performed on the modalities 3 or the devices 8 themselves. The latter relates, for example, to the computing power-intensive processing of 3D image data (volume data) of the respective modality 3 for storage (preprocessing) and/or the derivation of rendered views V (scenes or scene graphs) for the two-dimensional visualization (image synthesis, volume rendering) of such volume data.

Figure 2:
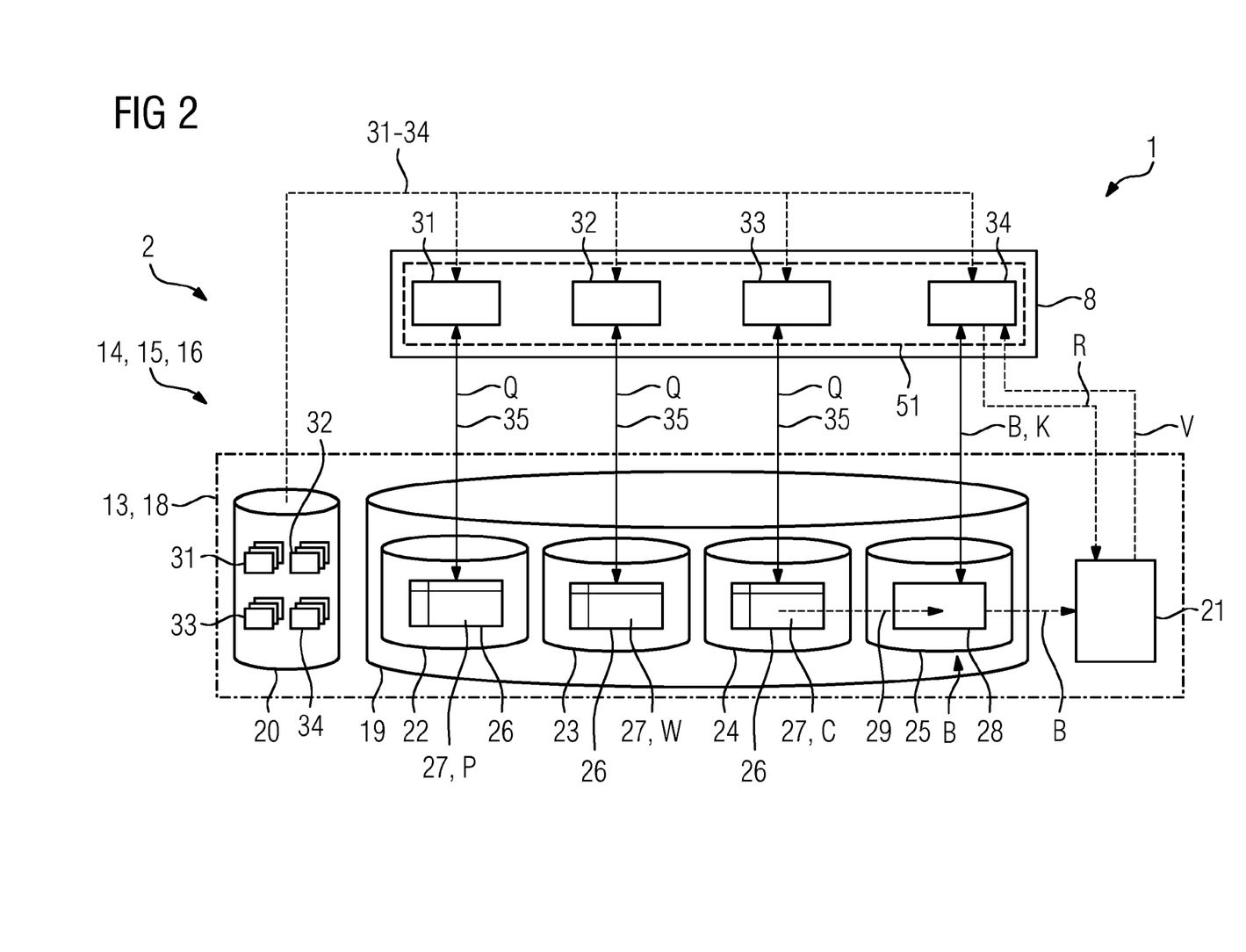
FIG. 2 shows in a schematic block diagram the software-related construction of the system.

FIG. 2 shows in a schematic block diagram the software-related construction of the system, according to which the system has specifically associated memory areas (hubs) in each case for different types of data of the medical facility in a cloud storage of the public cloud, namely a patient hub for patient data sets, a worklist hub for tasks, a context hub for context data sets and an image hub for image data sets, and wherein for each hub the system contains on each device an associated application for access to the data sets stored in this hub, wherein the first three hubs mentioned a table storage is set up in each case, contained in which is a table entry (tweet) associated with each data set of the hub, and wherein each application is configured to search through (browsing) the table storage of the associated hub and to extract and display a results list (feed) of selected tweets, and wherein the application associated with the image hub is configured to display (viewing) the image data sets.

According to FIG. 2 the data to be managed and edited within the framework of the facility 2 includes patient data sets P, tasks W, context data sets C and image data sets B, wherein this data, in detail, in each case has the contents described above in more detail. Image data sets B may contain medical image data or volume data or other image, sound, graphics or text information (photos, videos, documents).

According to FIG. 2, a separate memory area, which is hereinafter called a (resource) hub, is set up in each case for each of these different types of data (resources) within the cloud storage 19. A (patient) hub 22 for storage of the patient data sets P, a (worklist) hub 23 for storage of the tasks W, a (context) hub 24 for storage of the context data sets C, and an (image) hub 25 for storage of the image data sets B are therefore set up in the cloud storage 19.

Each of the hubs 22-24 contains a table storage (hereinafter called table storage 26).

Within the framework of the system 1, a table entry, which is hereinafter called a tweet 27, is set up for each stored data set in the table storage 26 of the respectively associated hub 22-24.

In the case of data sets, which by their nature include comparatively few discrete details, the entire data set is stored as a tweet 27 in the table storage 26 of the respective hub 22-24. In the example according to FIG. 2, this relates to the patient data sets P, tasks W, and context data sets C.

Instead of table storage 26, the worklist hub 23 may also have what is known as queue storage, however, for storage of the tasks W according to a First-in-first-out principle.

For storage of the image data sets B, which, as a rule, are essentially formed from a relatively large and usually non-alphanumeric data block, what is known as blob storage 28 is provided in image hub 25 instead of table storage 26. One context data set C respectively in the form of a tweet 27 is stored in the context hub 24 for the image data sets B stored in the image hub 25. This tweet 27 contains at least one Uniform Resource Identifier (URI) 29 that denotes the storage location of the image data set B in the blob storage 28 of the image hub 25.

For each of the hubs 22-25 an application 31-34 is provided in the App Store 20, and in each case this is selectively used for displaying and editing the data sets stored in the respectively associated hub 22-25. Each of the applications 31-34 therefore represents the associated hub 22-25 at the level of the device 8. Applications 31-34 are therefore also called "application hubs"—in the style of the resource hubs.

The applications provided in the App Store 20 therefore include an application 31 for managing and editing the patient data sets P stored in the patient hub 22, an application 32 for managing and editing tasks W, an application 33 for managing and editing context data sets C, and an application 34 for displaying and editing the image data sets B stored in the image hub 25.

The applications 31-34 may be downloaded from the App Store 20 onto each of the devices 8 and be executed there. If the system 1—as shown in FIG. 1—includes different types of devices (e.g., personal computers 9, tablet computers 11 and/or smartphones 12), different versions of the applications 31-34 are provided in the App Store 20 in each case, and these are adapted to run on the respective device 8.

For example, the applications 31-34 for running on the tablet computer 11 and the smartphone 12 are provided in the form of an app adapted to the respective device type, whereas the versions of the applications 31-34 provided for the personal computer 9 are designed to run in an Internet browser.

Compared to a conventional IT structure for managing medical data, from the user's perspective the patient hub 22 and the associated application 31 essentially assume the function of a conventional hospital information system (HIS). For example, all of the personal (and data protection-relevant) patient data is recorded in the patient hub 22, which therefore maps an electronic patient file for the individual patient. The remaining hubs 23-25 may not contain any information that could be intrinsically matched to a specific patient (Privacy Information). The worklist hub 23 and the associated application 32 present themselves to the user essentially as an equivalent to a conventional Radiology Information System (RIS) in that they list the tasks within the facility 1 that are pending implementation. From the user's perspective the context hub 24 and the associated application 33 essentially assume the function of a conventional PACS in that the information required for locating and processing image data sets B is stored and may be searched. Finally, the image hub 25 and the associated application 34 essentially assume the function of a conventional AV system.

Although the functions contained in the hubs 22-25 and the associated applications 31-34 are linked to each other to a high degree, each of the hubs 22-25 may also be operated together with the respectively associated application 31-34 independently of the other hubs 22-25 in each case and their applications 31-34. Therefore, for example, an image data set B contained in the image hub 25 may also be accessed without the associated context data set C of the context hub 24 if the application 34, associated with the image hub 25, makes available in some other way, e.g. by email, SMS or Twitter, the URI 29 of the image data set B to be displayed. Furthermore, the patient data P can also be held available outside of the public cloud 13 since the patient hub 22 is not necessary for the function of the remaining hubs 23-25 and associated applications 32-34.

A core element of the application 31 associated with the patient hub 22 is what is known as a browsing function that searches through the table storage 26 of the patient hub 22 for tweets 27 that correspond to a specific search term that may be predefined by a user. In response to a search query Q (FIG. 2) of the application 31 a results list, hereinafter called a feed 35, containing the tweet 27 corresponding to search query Q, is returned by the patient hub 22 to the application 31. The application 31 shows the obtained feed 35 on the device 8 on a page 36 of a graphic user interface 37 shown by way of example in FIG. 3.

Figure 3:
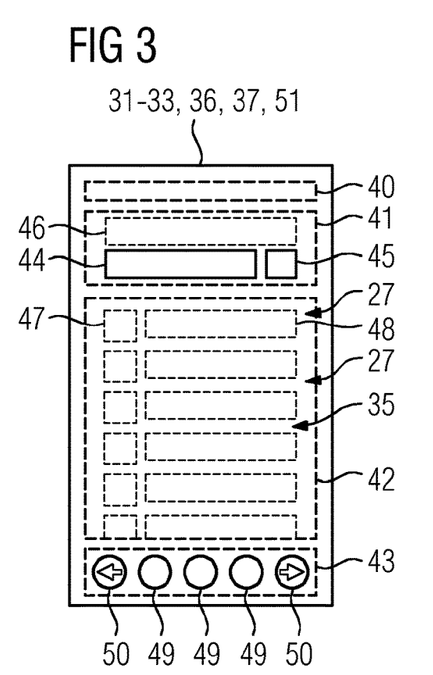
FIG. 3 shows in a schematic view one page of a user interface of an application intended to run on a smartphone, which is used to display a feed of the respectively associated hub.

In the exemplary embodiment according to FIG. 3, the page 36 essentially has four display areas with a different function, namely a header 40, a search field 41, a display field 42 and a task bar 43. The hub 22-24 with which the application 31 is associated is named in the header 40. In the example of application 31, the header 40 is therefore labeled e.g. with the word "patient hub". Furthermore, the facility 2 with which the system 1 is associated may be named in the header 40.

The search field 41 contains an input line 44 by way of which an alphanumeric search term can be input, and a button 45, activation of which by a user may start a search query Q on the basis of the search term input in the input line 44 beforehand.

Additionally or alternatively, the search field 41 contains a pre-selection field 46 by way of which the one or more preset search term(s) may be chosen by touching (in the case of a touch-sensitive screen) or clicking with an optionally present pointer.

The search terms that may be generated by the pre-selection field 46 are, for example, frequently used search procedures. For example, in the case of the application 31 corresponding to the patient hub 22, the pre-selection field 46 enables a pre-selection as to whether all tweets 27 ("all") or only those tweets 27 relating to patients for whom examinations are scheduled ("scheduled") or only those tweets 27 relating to patients for whom the recent service has already been billed ("billed")

should be returned as feed 35.

Optionally it is provided that, when generating a search term by way of the pre-selection field 26, an alphanumeric equivalent of this search term is automatically displayed in the input line 44.

The feed 35 returned on the basis of a search query Q is displayed in the display field 42. The display field 42 therefore contains in the form of a list those tweets 27 that have been found in the patient hub 22 on the basis of the search query Q of application 31. For example, a reduced image 47 and/or a keyword 48 is/are displayed for each tweet 27. Therefore, in the case of application 31 associated with the patient hub 22, a reduced image of the patient and the name of the patient, and optionally a patient identification number, may be displayed for each displayed tweet 27.

The search query Q, and the feed 35 returned on the basis of this, may be interactively changed by a user.

The search is defined on the basis of syntax according to REST or Open Data Protocol Standard (OData). It is basically similar to a WHERE condition according to the SQL standard, but in contrast to the latter is not dependent on a static re-indexing. For example, the tables of a hub do not require any index elements for the search, for which reason no re-indexing is required either, and accordingly no separate data servers or database servers have to be held available.

A user may select a tweet 27 by simply touching or clicking a tweet 27 displayed in the display field 42.

The task bar 43 contains a number of buttons 49 and 50, on activation of which by a user elementary operations for controlling the user interface 37 and for managing and editing the displayed feed 35 may be performed.

In the version shown in FIG. 3, application 31 is optimized for display on the smartphone 12. Only a single page 36 with a single feed 35 is ever displayed on the smartphone 12 at any one time. However, a plurality of instances of the page 36 or a plurality of instances of the entire application 31 may be generated simultaneously, wherein these instances are implemented concurrently on the smartphone 12 in the background of the display. Therefore, for example, a plurality of search queries Q may be processed at the same time as each other. The application 31, or optionally a plurality of instances of the application 31, may run in a generic container module 51 (or container) here. This container module 51 may be implemented, for example, as a separate application or as a plug-in for a Web browser. Alternatively, the application 31 may, however, also be designed to run directly in a Web browser, e.g. as an HTML5 application.

The buttons 50 in the task bar 43 make it possible to change between the running instances of the application 31 in that, when one of the buttons 50 is activated, the displayed page 36 of the user interface 37 is hidden and the corresponding page 36 of a different instance of the application 31 is displayed.

Figure 4:
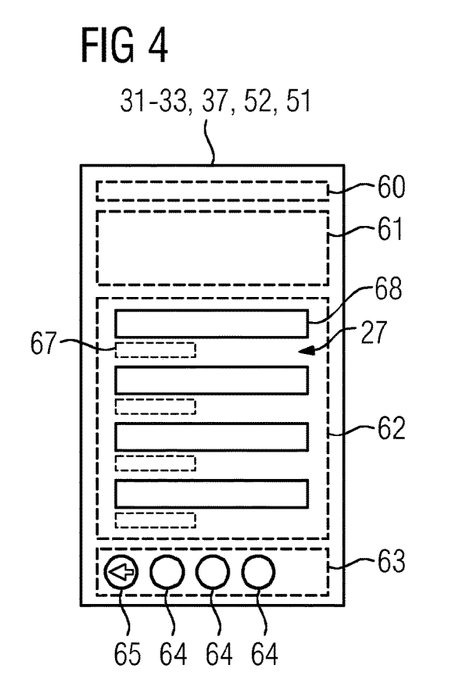
FIG. 4 shows in a view according to FIG. 3 a further page of the user interface of the application there, which is used to display a tweet of the associated hub.

In one embodiment, the following functions are allocated to the further buttons 49 of command line 43:

"Create"—in response to activation of the corresponding button 49, a new page 36 of the user interface 37 is generated, optionally together with a new instance of application 31;

"Delete"—in response to activation of the corresponding button 49, the displayed page 36 of the user interface 37 is ended, optionally together with the associated instance of application 31; and "Read"—in response to activation of the corresponding button 49, a further page 52—schematically shown in FIG. 4—of the user interface 37 is opened in which the data content of the selected tweet 27 is displayed simply for viewing or for changing.

According to FIG. 4, page 52 likewise includes four regions, namely a header 60, heading field 61, display field 62 and a task bar 63.

The header 60 has—analogously to the header 40 on page 36—the associated hub 22-24 and the facility 2. The heading field 61 identifies the type of the data set shown and in the case of application 31 therefore contains, for example, the word "patient" (or "patient entity").

The content of the selected tweet 27—in the case of application 31 the content of the (patient) data set therefore—is displayed in display field 62. In this case the field name 67 of the patient data set (for example "first name", "surname", "patient ID", "age", . . . ) together with the respective field content 68 (for example, in other words the specific first name, surname, the specific patient ID and the specific age of the patient) are displayed in display field 62.

The command line 63 contains buttons 64 to which the following functions are assigned: "Create"—in response to activation of the corresponding button 64, a new instance of page 52 is generated to set up a new tweet 27 and therefore a new (patient) data set P;

"Update"—in response to activation of the corresponding button 64, the—optionally altered—field contents 68 are stored by application 31 overwriting the displayed tweet 27 directly in the table storage 26 of the patient hub 22 with the altered details; and "Delete"—in response to activation of the corresponding button 64, the displayed tweet 27 is deleted by the application 31 directly in the table storage 26 of the patient hubs 22 and the displayed page 52 is closed.

The command line 63 also contains a button 65 on activation of which application 31 closes the displayed page 52 without changing the tweet 27, and displays the underlying page 36 again.

The command lines 43 and 63 may have further buttons for commands. Similarly, one or more of the function(s) described using the buttons 49, 50, 64 and 65 may also be associated with one of the optionally present electromechanical buttons of the smartphone 12. The respective button is in this case may be removed from the command line 43.

The applications 32 and 33 each have a browsing function that corresponds to application 31. For example, the respective user interface 37 of applications 32 and 33 in each case also has the pages 36 and 52 described with reference to FIGS. 3 and 4.

However, applications 32 and 33 access the worklist hub 23 or the context hub 24 and are adjusted accordingly. Therefore, in one example the tweets 27 displayed within the framework of application 32 contain details on a specific task W (for example details on the appointment date of the task, the department entrusted with the task, and details on the task itself and the task flow in which this task is optionally incorporated), and the tweets 27 displayed within the framework of application 33 contain the content of one context data set C respectively (e.g., details on the document type, storage location, data format and optional recording parameters for an image data set B).

Application 34, on the other hand, is used for displaying ("viewing") the non-alphanumeric content of an image data set B stored in the image hub 25. For this the graphic user interface 37 of application 34 includes a page 69 shown in FIG. 5. Like page 52, page 69 also contains a header 70, heading field 71, display field 72 and command line 73. The heading field 71 specifies, for example, the type of image data set B displayed (e.g. as "2D viewing", "3D viewing", "media viewing", "document viewing", etc.). The visual content of the image data set B, i.e., for example the image, volume, video or text document, is displayed in display field 72. In addition to button 65, the command line 73 contains further buttons 74 for influencing the display, for example for enlarging or reducing the data content displayed in display field 72 or to shift a displayed image detail. In addition, a button 74 can be provided for deleting an image data set B.

Figure 5:
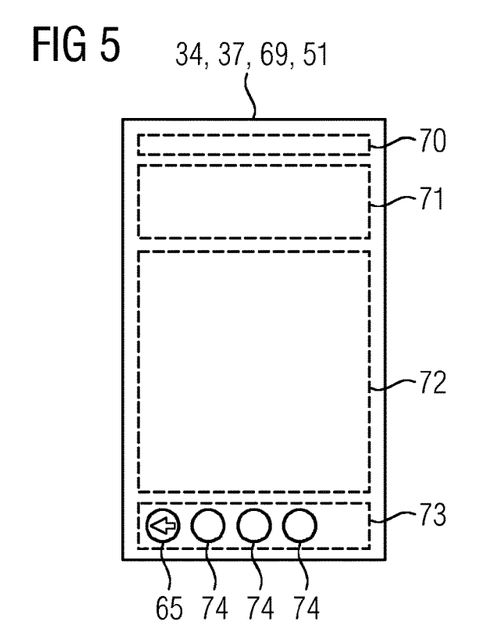
FIG. 5 shows in a view according to FIG. 3 a page of the user interface of the applications associated with the image hub, which is used to display the image information of an image data set.

Instead of the shared page 69 for displaying different types of data, application 33 may also include different viewing pages that are each configured to display a specific type of document (image, volume, video, text document, etc.).

In respect of the display of volume data (3D viewing), application 34 may be operated in two operating modes, namely in a "device only mode" in which the computing steps required for displaying the volume data on the two-dimensional screen (e.g., the preparation of rendered views V) are performed on the device 8 itself, and a "cloud service mode" in which application 34 requests cloud compute services 21 for these computing operations by way of an appropriate query R (FIG. 2).

In device only mode application 34 directly accesses the image data sets B stored in the blob storage 28 of the image hub 25. In cloud service mode the image data B is edited by cloud compute services 21, wherein only the resulting two-dimensional views V are supplied by the cloud 13 to application 34. Owing to appropriate pre-adjustment, application 34 works innately in cloud service mode and only switches to device only mode if the network connection to the public cloud 13 falls below a predefined minimum quality.

In one embodiment, application 34 may also contain functions for editing the image data (e.g., for measuring and/or segmenting image structures and/or for introducing markings and/or annotations). To aid medical diagnosis of the displayed image data, application 34 also contains a function for creating what is known as a key image K (FIG. 2). As mentioned above, this is a snapshot, in other words a copy of the image information of the displayed image detail. On a corresponding user command, application 34 is configured to store created key images K directly as image data set B in the blob memory 28 of the image hub 25.

Applications 32-34, or optionally a plurality of instances of these applications 32-34, likewise may run(s) in the container module 51. As schematically indicated in FIG. 2, one shared container module 51 may be provided for all applications 31-34. Alternatively, a separate container module may be associated with each application 31-34, however.

Communication between each of the hubs 22-25 and the respectively assigned application 31-34 is configured such that it is compatible with the REST (Representational State Transfer) principle customary in Internet data communication. For example, the data exchanged between the hubs 22-25 and the respective application 31-34 satisfies standards XML, JSON and ATOM. Image data B is stored in the image hub 25 in, for example, JPEG format, and volume data may be stored in DICOM format. The views V (scene graphs) of volume data optionally provided by the public cloud 13 to application 34 may be created in JPEG format.

For direct access to the data stored in the respective hub 22-25 each application 31-34 uses a multiply instantiable cloud driver that is present in the form of an Application Program Interface (API).

When instructed by the user, each of the applications 31-33 is configured to externalize feeds 35 from the associated hub 22-24 into a local memory of the device 8. This way, the feeds 35 and the tweets 27 contained therein may be displayed and/or edited by application 31-33 even without a network connection to the public cloud 13. Furthermore, on the user's command, each application 31-33 is configured to transfer externalized feeds 35 or tweets 27 to a different instance of the same or a different application 31-34. For the internal transfer of the feeds 35 or tweets 27, a local memory area called an "exchange board" is configured in the memory of the device 8 to jointly access all instances of applications 31-34. For exchange via the exchange board the feeds 35 or tweets 27 to be exchanged are serialized in XML/JSON files that are stored in the local memory of the device 8 and are then deserialized again. To exchange feeds 35 and tweets 27 between different devices 8 the applications 31-34 may have interfaces for Twitter or an email program.

Figure 6:
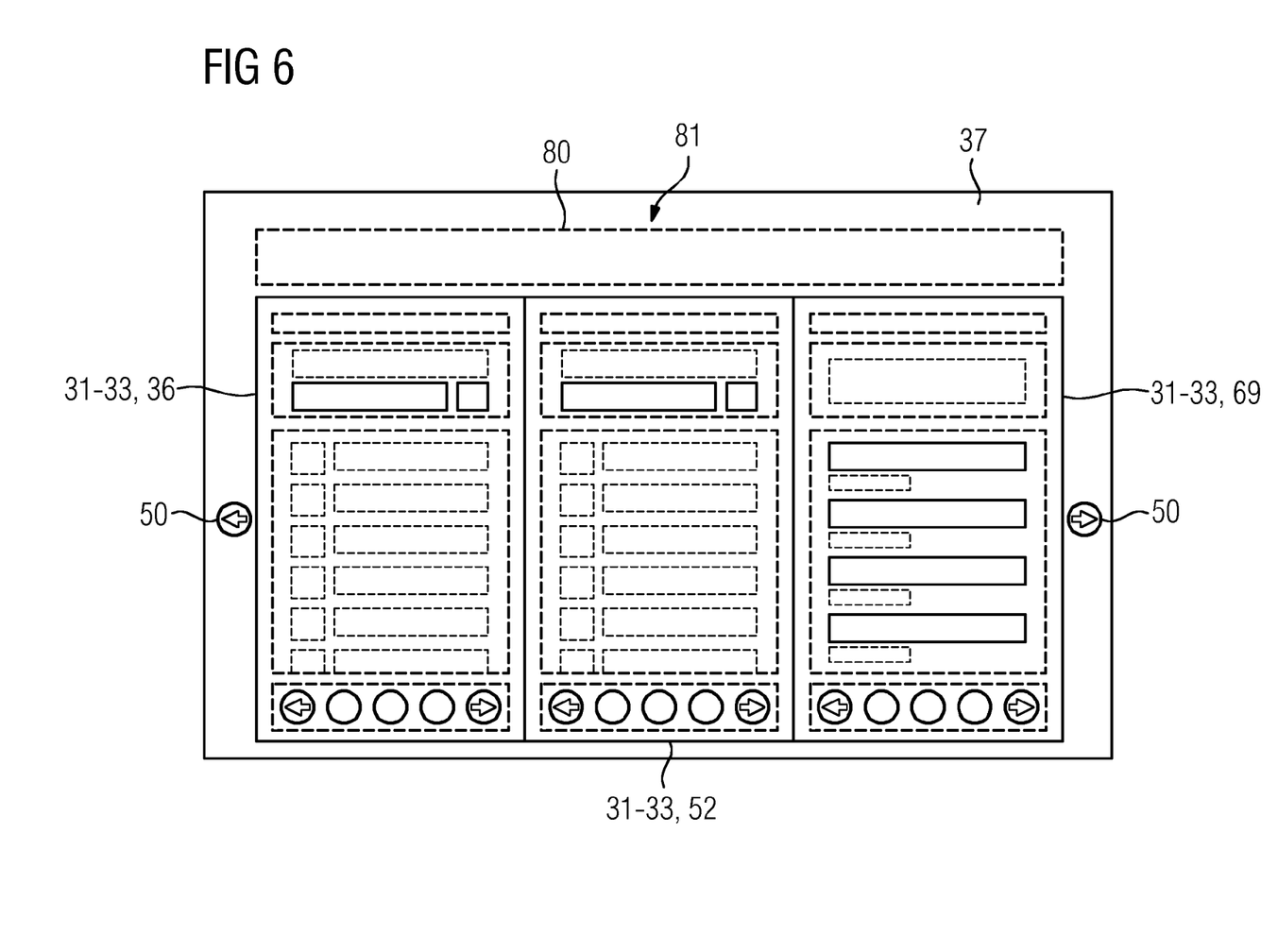
FIG. 6 shows in a view according to FIG. 3 a variant of the application there which is intended to run on a personal computer, notebook or tablet computer, in which a plurality of pages of the user interface can be displayed at the same time.

FIG. 6 shows a variant of applications 31-33, wherein the user interface 37 is optimized for display on a large-format screen, for example the screen 10 of the personal computer 9 or the screen of the tablet computer 11. The user interface 37 according to FIG. 6 differs from the user interface 37 shown in FIGS. 3 and 4 essentially in that a plurality of instances of applications 31-33 and the corresponding pages 36 and/or 52 of the user interface 37 may be seen side by side (and therefore simultaneously).

In the view according to FIG. 6 the user interface 37 also has additional navigation buttons 50, on activation of which displayed pages 36 and/or 52 may be scrolled through again.

The user interface 37 also has a menu line 80, on activation of which it is possible to change between the various applications 31-34. The menu line 80 is, for example, a component of a container module 81 (or container) in which the existing instances of applications 31-34 run.

Figure 7:
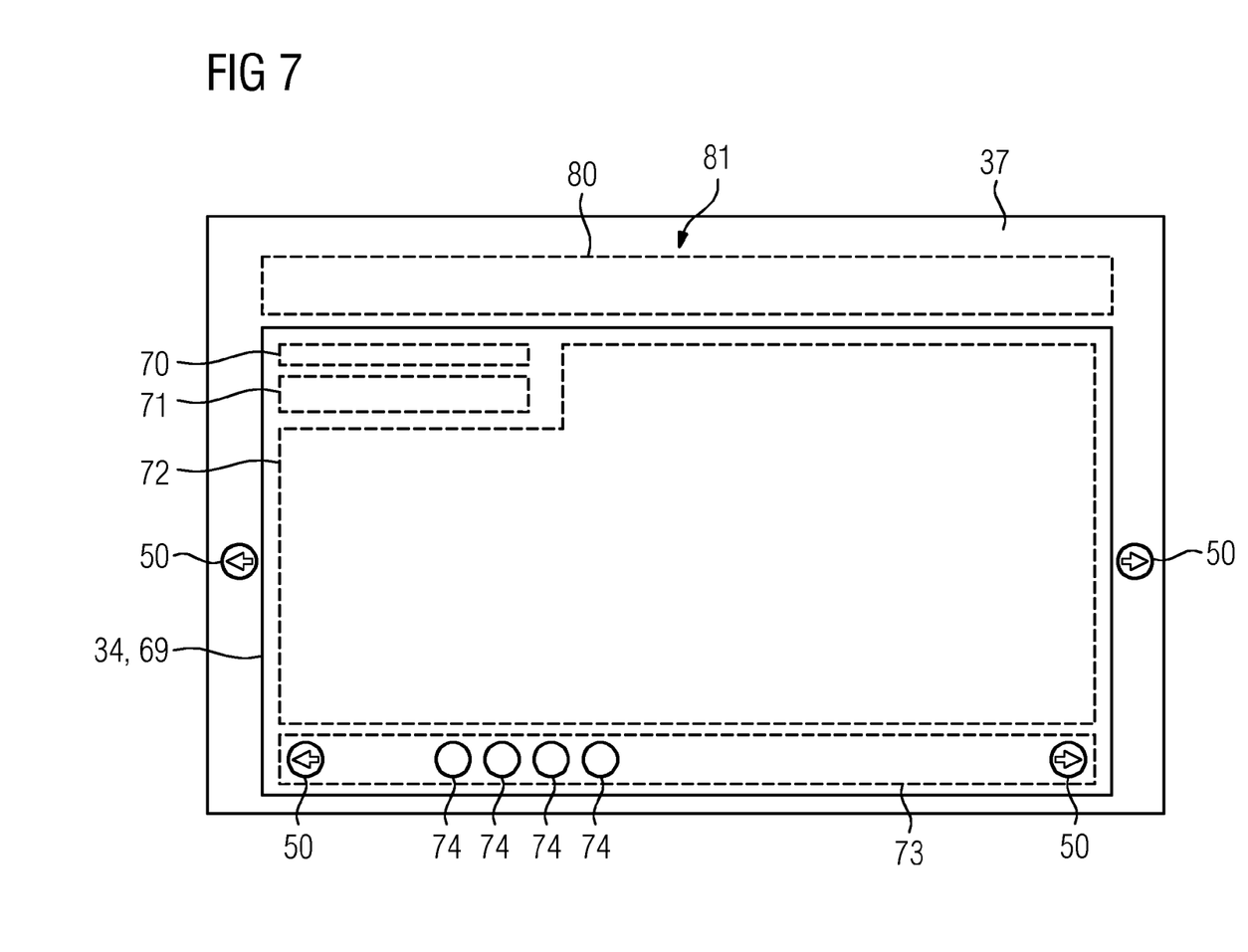
FIG. 7 shows in a view according to FIG. 6 a further page of the user interface which is used to display the image information of an image data set.

FIG. 7 shows a version of page 69 of application 34 optimized for display on a large-format screen, in which the display field 72 fills almost the entire screen area.

Figure 8:
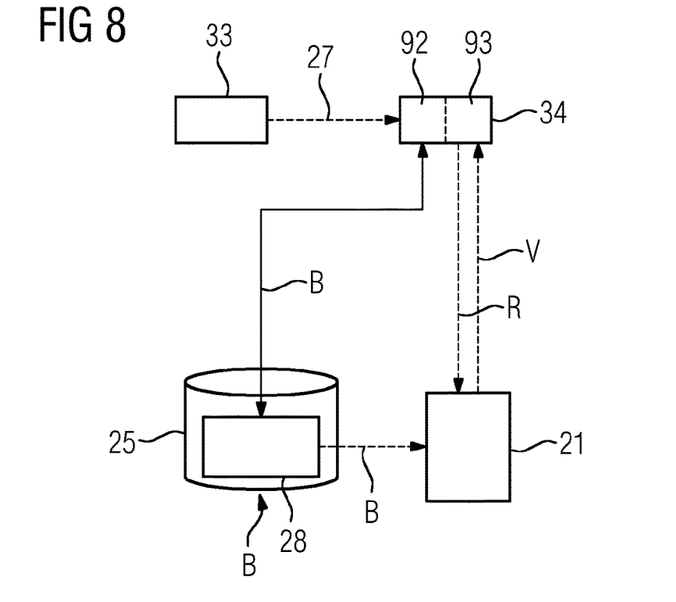
FIG. 8 shows in a schematic block diagram an alternative embodiment of the system in which the viewing application associated with the image hub contains separate modules for displaying 2D image data and volume data.

FIG. 8 shows a variant of the system 1 in which the application 34 for displaying 2D image data and volume data contains a (2D viewing) module 92 and a (3D viewing) module 93 dependent hereon. Application 34 may also run in a limited version with just one of the modules 92 or 93. To download the image data set B for display the 2D viewing module 92 always directly accesses the blob storage 28 of the image hub 25. The 3D viewing module 93 either likewise directly accesses the volume data stored in the image hub 25 or uses cloud compute services 21 to create the views V.

To display a specific image data set B using application 34, for example the associated tweet 27 is ascertained from application 33 associated with the context hub 24 and is transferred via the exchange board to application 34. Using the URI 29 contained in the transferred tweet 27, application 34 loads the image data set B from the image hub 25.

Figure 9:
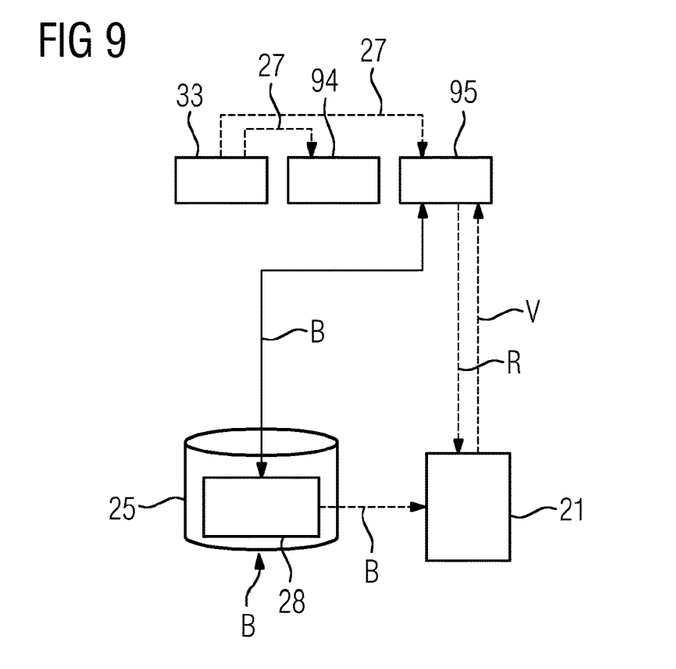
FIG. 9 shows in a view according to FIG. 8 a further embodiment of the system, wherein two stand-alone applications are allocated to the image hub, namely a 2D viewing application for displaying 2D images and a 3D viewing application for visual display of volume data.

FIG. 9 shows a further variant of the system 1 in which a 2D viewing application 94 and a 3D viewing application 95 dependent hereon are associated with the image hub 25 instead of the individual application 34.

Figure 10:
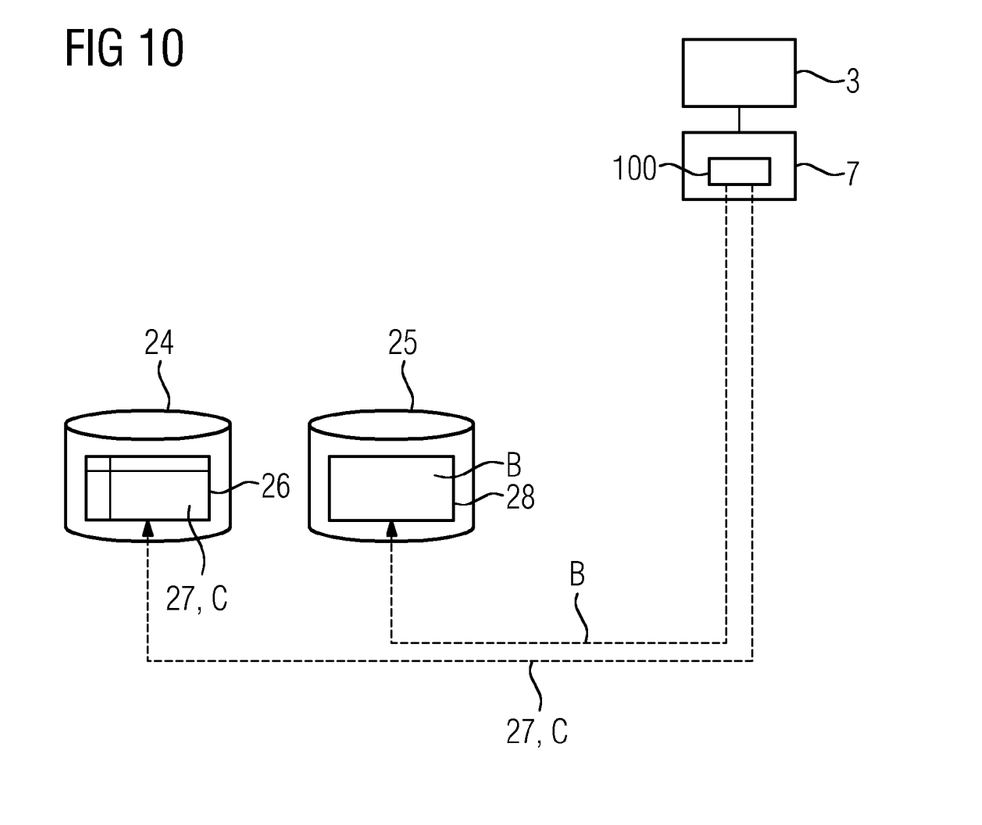
FIG. 10 shows in a view according to FIG. 8 a further embodiment of the system in which a modality is fitted with a storage driver for loading image data directly into the image hub of the cloud storage.

According to FIG. 10 each modality 3 of the system 1 is provided with a storage driver 100 implemented in the computer 7. The storage driver 100, which is in the form of an Application Program Interface (API) for the control and evaluation software of modality 3, is configured to directly (without using cloud compute services 21) write an image data set B, created by modality 3 and transferred to the storage driver 100, in the blob storage 28 of the image hub 25. The storage driver 100 also sets up an associated context data set C as tweet 27 into the table storage 26 of the context hub 24.

In one embodiment, the storage driver 100 converts the image data (at least if the image data is 2D image data) into the JPEG format if the modality 3 originally creates the image data in a different data format. In the case of volume data, this, on the other hand, may be stored in the blob memory 28 of the image hub 25 in DICOM format.

Furthermore, the storage driver 100 optionally performs further data pre-processing processes (preprocessing) before it stores the image data set in the image hub 25.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for managing and editing data of a medical firewall facility, the method comprising:
    providing separate memory areas in a cloud storage of a public cloud for at least two different types of medical data sets, respectively;
    storing the at least two different types of medical data sets in the separate memory areas in the public cloud such that a medical data set of the at least two different types of medical data sets is directly accessible from the Internet by a user device when a subscription associated with the respective memory area of the separate memory areas in the public cloud exists, wherein table storage is provided inside at least one memory area of the separate memory areas, and wherein, inside the table storage, a table entry is associated with each data set stored in the at least one memory area and contains the associated data set;
    providing at least one application for running on the user device, the at least one application being specifically associated with each memory area of the separate memory areas, respectively;
    returning, in response to a direct search of content of the table storage using an application of the at least one application associated with the at least one memory area, a results list, such that selected table entries are extracted in the results list;
    externalizing, using the application, the results list from the associated memory area of the public cloud into a local memory of the user device,
    wherein the subscription is associated with the user device and defines which of the separate memory areas is accessible to the user device via the at least one application, and
    wherein the at least one application is configured to retrieve, display, or retrieve and display the data sets contained in the respective memory area of the separate memory areas based on the subscription.

2. The method of claim 1, wherein the separate memory areas comprise at least two memory areas of:
    a patient memory area in which each data set contains personal and medical data about a specific patient;
    a work list memory area in which each data set contains a task or sequence of tasks that is to be carried out by a medical user;
    an image data memory area in which each data set contains image data; and
    a context memory area in which each data set contains context formation about an image data set.

3. The method of claim 1, wherein a data set contained in the respective memory area of the separate memory areas is directly accessed by one or more applications of the at least one application.

4. The method of claim 1, wherein a data set contained in the respective memory area of the separate memory areas is directly generated, edited, and deleted by one or more applications of the at least one application.

5. The method of claim 1, wherein one or more applications of the at least one application is operable in both a device only mode and in a cloud service mode,
    wherein in the device only mode, the data sets contained in the respective memory area are accessed and displayed solely by the one or more applications, and
    wherein in the cloud service mode, computing power of the public cloud is used for accessing, displaying, or accessing and displaying the data sets contained in the respective memory area.

6. The method of claim 1, wherein the results list is displayable, editable, transmittable, or any combination thereof to a different instance of the same application, or to a different application, by the application even without a network connection to the public cloud.

7. The method of claim 1, wherein a patient-specific image data set containing image data is generated and stored directly in the respective memory area of the cloud storage by a medical modality.

8. A system for managing and editing data of a medical facility, the system comprising:
    at least two memory areas set up in cloud storage of a public cloud, the at least two memory areas being configured to store at least two different types of data of medical data sets, respectively, wherein a specific type of data of the at least two different types of data of medical data sets is allocated to each memory area of the at least two memory areas, and wherein the medical data sets stored in the respective memory area in the public cloud are stored such that the data sets are accessible from the Internet by a user device when a subscription associated with the respective memory area in the public cloud exists, wherein at least one memory area of the at least two memory areas comprises a table storage, wherein, inside the table storage, a table entry is associated with each data set stored in the at least one memory area and contains the associated data set, and wherein content of the table storage is directly searchable by the one or more applications associated with the at least one memory area such that selected table entries are extracted in a results list; and
    at least one application specifically associated with each memory area of the at least two memory areas for running on the user device configured to retrieve and display the data sets contained in the respective memory area, wherein one or more applications of the at least one application is configured to externalize the results list from the respective memory area of the cloud storage into a local memory of the user device,
    wherein the subscription is associated with the user device and defines which of the at least two memory areas is accessible to the user device via the at least one application.

9. The system of claim 8, wherein the at least two memory areas comprise:
a patient memory area in which each data set contains personal and medical data about a specific patient;
a work list memory area in which each data set contains a task or sequence of tasks that is to be carried out by a medical user;
an image data memory area in which each data set contains image data;
a context memory in which each data set contains context information about an image data set; or
any combination thereof.

10. The system of claim 8, wherein one or more applications of the at least one application is configured to directly access the data sets contained in the respective memory area.

11. The system of claim 8, wherein one or more application of the at least one application is configured to directly generate, edit, and delete the data sets contained in the respective memory area.

12. The system of claim 8, wherein one or more application of the at least one application are operable in both a device only mode and in a cloud service mode,
wherein in the device only mode, the data sets contained in the respective memory area are accessed and displayed solely by the one or more applications, and
wherein in the cloud service mode, computing power of the public cloud is used for accessing, displaying, or accessing and displaying the data sets contained in the respective memory area.

13. The system of claim 8, wherein the results list is displayable, editable, transmittable, or any combination thereof to a different instance of the same application, or to a different application, by the application even without a network connection to the public cloud.

14. The system of claim 8, further comprising a storage driver implemented or implementable in a medical modality, the storage driver being configured to directly store an image data set, generated by the medical modality and containing patient-specific image data, in the respective memory area of the public cloud.

* * * * *